United States Patent [19]
Jordan

[11] Patent Number: 5,980,567
[45] Date of Patent: Nov. 9, 1999

[54] CONNECTING DEVICE FOR NATURAL ARTERIES WITH ARTIFICIAL ARTERIES

[75] Inventor: Gerhard Paul William Jordan, Millbrae, Calif.

[73] Assignee: Paul William Jordan, Millbrae, Calif.

[21] Appl. No.: 09/110,385

[22] Filed: Jul. 4, 1998

[51] Int. Cl.[6] .................................................... A61F 2/06
[52] U.S. Cl. ................................................ 623/1; 623/12
[58] Field of Search .......................................... 623/1, 12

[56] References Cited

U.S. PATENT DOCUMENTS

| | | | |
|---|---|---|---|
| 4,955,899 | 9/1990 | Della Corna et al. | 623/1 |
| 5,246,452 | 9/1993 | Sinnott | 623/1 |
| 5,480,434 | 1/1996 | Eckstein et al. | 623/11 |
| 5,609,624 | 3/1997 | Kalis | 623/1 |
| 5,653,744 | 8/1997 | Khouri | 623/1 |
| 5,700,287 | 12/1997 | Meyers et al. | 623/1 |
| 5,716,395 | 2/1998 | Meyers et al. | 623/1 |
| 5,728,131 | 3/1998 | Frantzen et al. | 606/194 |
| 5,747,128 | 5/1998 | Campbell et al. | 428/35.7 |

OTHER PUBLICATIONS

Frank J. Veith, McGraw Hill, 1994, Biologic and Prosthetic Materials for Vascular Conduits, p. 532, Vascular Surgery 2nd Edition.

Frank J. Veith, James A. Deweese, 1982, Critical Problems in Vascular Surgery, p. 151, Anastomotic Neointimal Fibrous Hyperplasia: Pathogenesis and Prevention.

*Primary Examiner*—David H. Willse
*Assistant Examiner*—Suzette J. Jackson

[57] ABSTRACT

The present invention discloses a connecting device to connect artificial arteries to normal arteries. The object of the invention is the prevention of obstruction of blood flow by hypertrophy of the inner lining of the artery commonly designated as the intima. The connecting device is placing the opening of the artificial artery inside of the natural artery beyond the level of the intima. This arrangement is preventing irritation of the intima of the natural artery by reducing turbulence of the boundary layer of the flowing blood. The connecting device can be manufactured as an integral part of the artificial artery or as a separate part to be connected to an artificial artery. The connecting device consists of a part penetrating the wall of the tapped natural artery and a sleeve to be attached to the outside of the natural artery. The sleeve itself is permanently attached to the connecting device. The distal part of the connecting device can be angled in order to facilitate the desired direction of the implanted artificial artery.

12 Claims, 3 Drawing Sheets

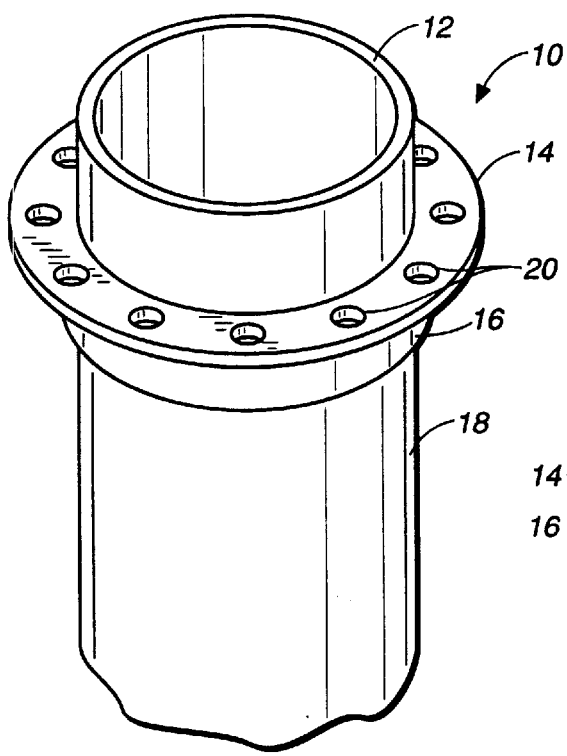
FIG._1
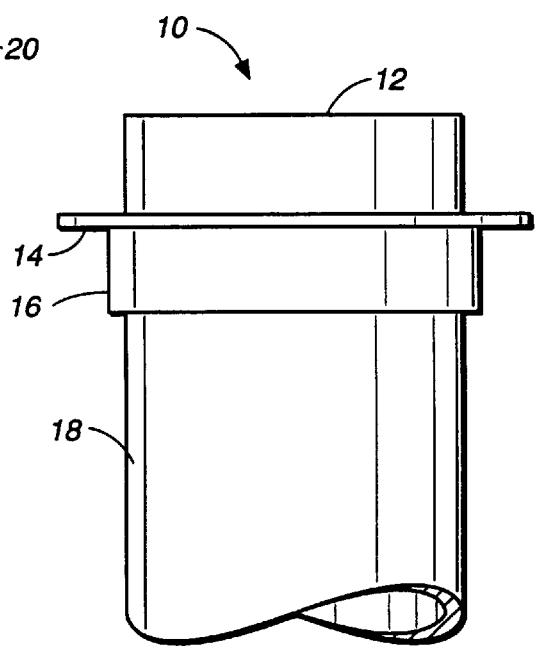
FIG._2
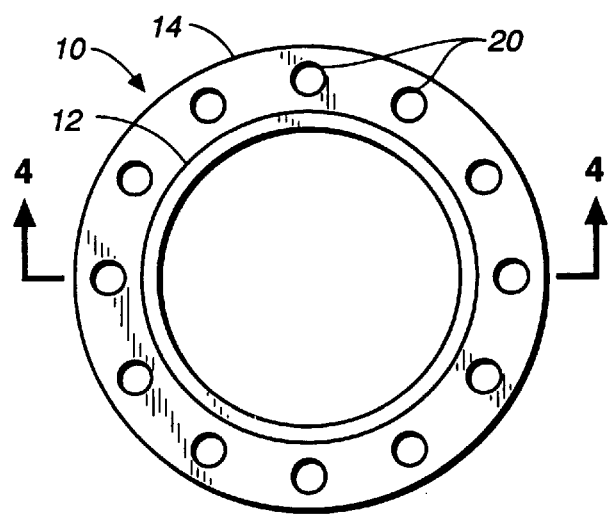
FIG._3

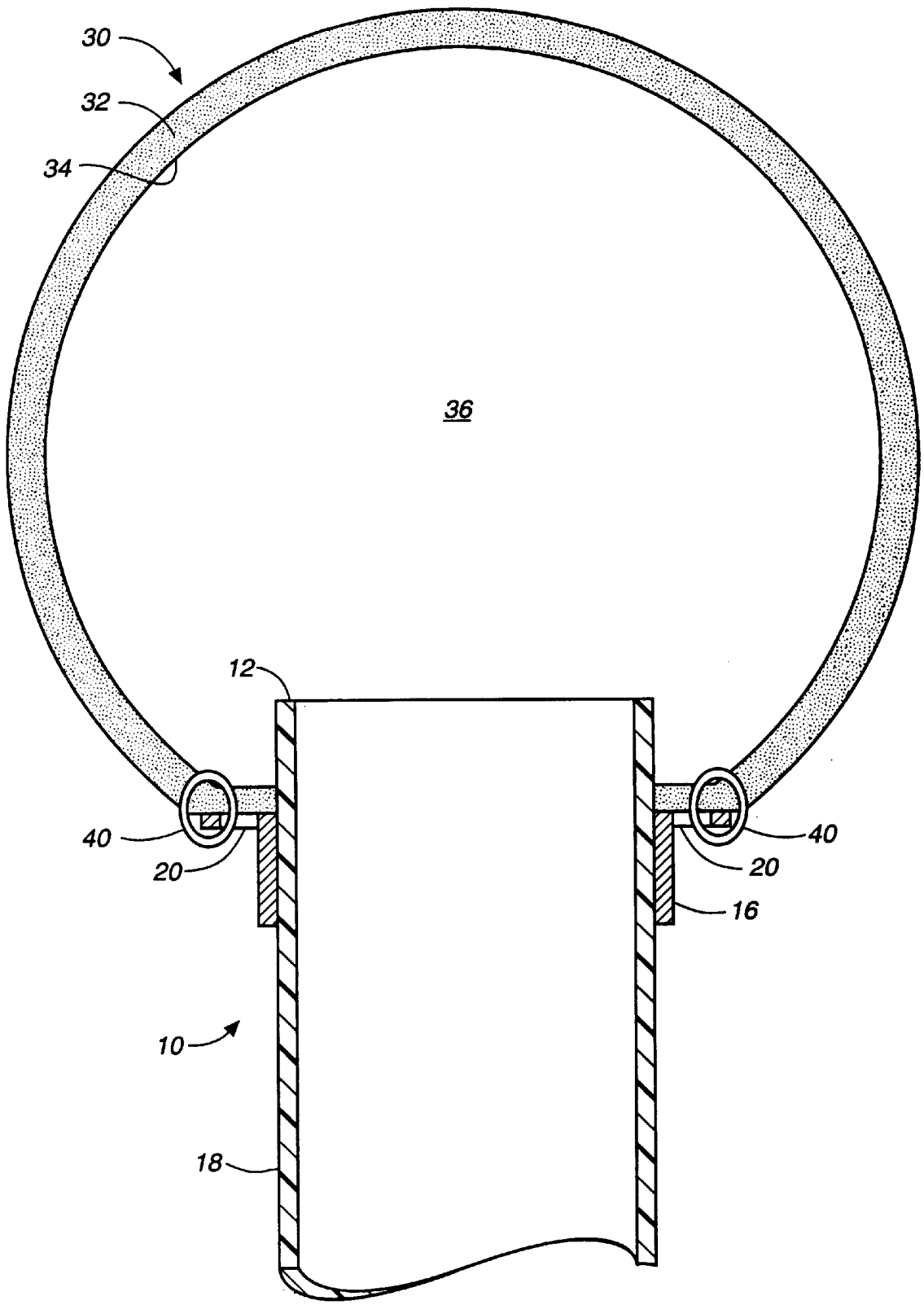
FIG._4

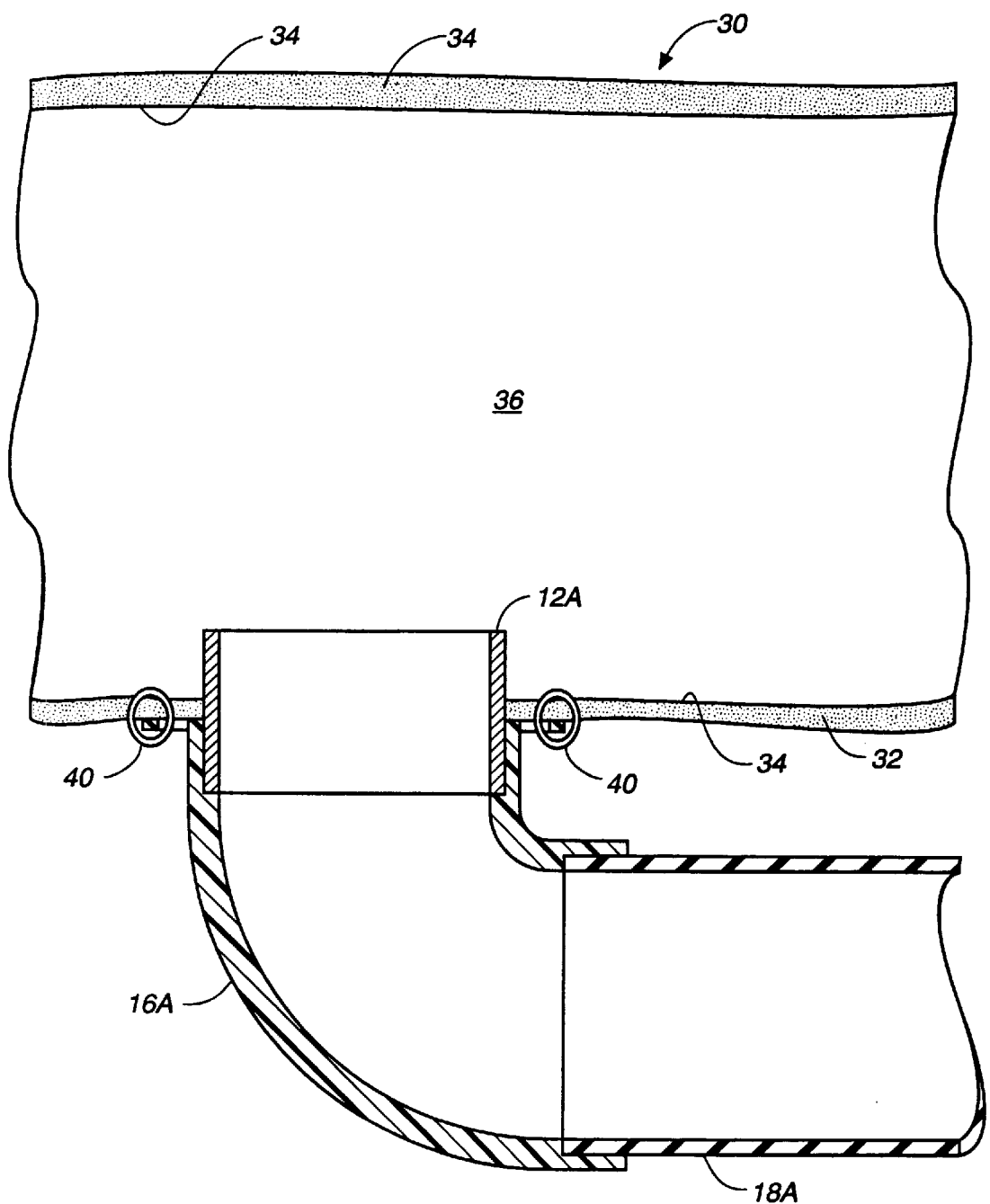
FIG._5

CONNECTING DEVICE FOR NATURAL ARTERIES WITH ARTIFICIAL ARTERIES

BACKGROUND—FIELD OF THE INVENTION

This invention relates to the connection of artificial arteries or grafts to natural arteries, specifically the end to side connection whereby the end of the artificial artery is connected to the side of the natural artery.

BACKGROUND OF THE INVENTION

Vascular grafts and artificial arteries are well known in the art. See for example, U.S. Pat. No. 5,747,128 to Campbell, Chastain, Alvaro, and Pond; U.S. Pat. No. 5,716,395 to Myers and Lewis; U.S. Pat. No. 5,700,287 to Myers, Lewis, and Campbell; U.S. Pat. No. 5,609,624 to Kalis; U.S. Pat. No. 5,246,452 to Sinnott; and U.S. Pat. No. 4,955,899 to Della Corn, Farnan, Colone, and Kowligi. Artificial arteries are useful for bypassing obstructed natural arteries. All of these prior arts do not address the fact that the end to side connection of artificial arteries to natural arteries are subject to possible obstruction due to the hypertrophy of the intima caused by fluid dynamics in the region of the junction.

The junction between natural artery and an artificial artery in side to end fashion is usually carried out in the following manner. For side to end connections, surgeons accomplish the junction of natural artery to artificial vessel by forming an opening in the natural artery to be fitting the proximal opening of an artificial vessel. Surgeons commonly connect artificial arteries to natural arteries by suturing the end of the wall of the artificial artery to the side of the wall of the natural artery. The differences of natural artery to artificial artery in their respective properties make it unavoidable that the dynamics of the blood flow constantly irritate the intima of the natural artery at the junction. The irritation is leading to hypertrophy of the arterial intima thereby narrowing the proximal orifice of the artificial vessel. At this junction the innermost layer of the natural artery, which is called "intima" in medical terms, is proliferating to such a degree that often blood flow into the artificial artery is diminished or cut off completely. Surgeons try to prolong the functioning of said junction by making the orifice of the junction as large as possible. In order to mitigate the problem surgeons prefer to connect the artificial artery at an angle. This approach is commonly called "fishmouthing". The connection of the artificial artery to the natural artery at an angle is providing a larger opening at the side of the natural artery and is, therefore, giving more space to the proliferating intima in order to prolong patency of the opening of the artificial artery. According to the authoritative textbook of Vascular Surgery 2nd Edition by Frank J. Veith, McGraw Hill 1994, *Biologic and Prosthetic Materials for Vascular Conduits*, Chapter 39, Page 532, Line 49 (Exhibit 1), "small grafts fail at a rate approaching 100,000 per year in the United States alone". Continuing on the same page, Line 55, "the biology of the human endothelial cell and its role in maintaining blood fluidity remain major areas requiring investigation".

The problem of "Neointimal Fibrous Hyperplasia: Pathogenesis and Prevention" is discussed in *Critical Problems in Vascular Surgery*, by Frank J. Veith, MD., printed by Appleton Century Crotts, New York, 1982 on Page 151 by James A. Deweese. On page 152, line 1 to 4, (Exhibit 2), "As long as the cause and the prevention of neointimal fibrous hyperplasia at anastomoses as well as along the entire graft surface remains undetermined, the search for the ideal vascular graft will continue."

The surgical practice as described above does not take into account the mechanics of fluid dynamics, specifically micro whirls caused by the flow of blood, which is a suspension of microscopic particles in a viscous fluid. The present practice of anatomizing (connecting) of tubing with different mechanical properties is also neglecting the fact that the flow of any liquid, especially of a liquid with a considerable viscosity, is layered whereby the central core layer is moving at the fastest rate. The very purpose of the intima is to accommodate laminar flow. This pattern of flow is unduly disturbed by the usual side to end connection used presently in vascular surgery. The fluid dynamic forces unleashed by this technique have a negative effect on the intima at the site of the connection. The blood and the red blood cells in particular, due to their heavier specific weight, are scraping the intima sidewise and even hit it head on at the downstream end of the connection causing the intimate to proliferate and obstruct flow.

There is thus a need for a connecting device which does not promote the obstruction of the blood flow into the artificial artery.

SUMMARY OF THE INVENTION

The object of the invention is the prevention of the hypertrophy of the intima usually seen at the surgical connection. This object can be achieved by diverting the flow of the blood from the inside of the natural artery. This can be accomplished by inserting part 1 of the connecting device (FIGS. 1 and 2) into the lumen of the natural artery through an incision into the wall of the artery. The insertion is done in such a fashion that the sleeve is touching the outside of the natural artery and is thereby determining the position of the orifice of the artificial artery within the flowing blood. The sleeve itself is sutured to the outside of the natural artery to be tapped. The use of this connecting device will prevent hypertrophy of the intima.

DESCRIPTION OF THE DRAWINGS

FIG. 1 is a perspective view of the connecting device.

FIG. 2 is a front view of the connecting device.

FIG. 3 is a top view of the connecting device.

FIG. 4 is a cross-sectional view taken along line 4—4 in FIG. 3 as it would appear attached to an artery.

FIG. 5 is a cross-sectional view of an alternative form of the invention, the connecting device with a bend in it, as it would appear attached to an artery.

NUMBER LIST

10 Connecting Device
12 Top Section (penetrating the wall of the natural artery beyond the intima)
14 Mid Section Sleeve
16 Attachment of Sleeve
18 Artificial Artery
20 Holes (or tissue to be penetrated by a surgical needle)
30 Natural Artery
32 Wall of Natural Artery
34 Inner Lining of the Natural Artery (commonly called the intima)
36 Lumen of the Natural Artery
40 Suture

DESCRIPTION OF THE PREFERRED EMBODIMENTS

The object of the invention is the prevention of the obstruction of blood flow by hypertrophy of the inner lining of the artery commonly designated as the intima. This object can be achieved by diverting the flow of the blood from the inside of the natural artery. This can be accomplished by inserting part 1 of the connecting device (FIGS. 1 and 2) into the lumen of the natural artery through an incision into the wall of the artery. The insertion is done in such a fashion that the sleeve is touching the outside of the natural artery and is thereby determining the position of the orifice of the artificial artery within the flowing blood. The sleeve itself is sutured to the outside of the natural artery to be tapped. The use of this connecting device will prevent hypertrophy of the intima. The connecting device is placing the opening of the artificial artery inside of the natural artery beyond the level of the intima. This arrangement is preventing irritation of the intima of the natural artery by reducing turbulence. The connecting device consists of a part penetrating the wall of the tapped natural artery and a sleeve to be attached to the outside of the natural artery.

The connecting device 10 can be manufactured as an integral part of the artificial artery or it can be produced separately in order to be connected to an artificial artery later. When the connecting device is made separately from the artificial artery there is a connecting arrangement between the connecting device and the artificial artery. Said connecting device 10 comprising a tube with an inlet opening (or receiving end) and an outlet opening and a sleeve positioned between said openings. The length of part 12 of the connecting device 10 should be long enough to reach through the natural artery wall 32 and into the lumen of the natural artery. (See FIGS. 1, 2, 4, and 5 part 12 and 12A.)

The sleeve as seen in FIGS. 1, 2, 3, 4 and 5 as part 14 is adjacent to and attached to the wall of the natural artery 32 seen in FIG. 4. FIGS. 1, 2, 3, and 4 show the sleeve itself is attached to part 18 by a reinforcing cuff part 16. FIG. 5 shows a possible variation that the attachment of the sleeve 16A is also providing a possible bend for the artificial artery 18A. The inside diameter of the said connecting device 10 is determined by the amount of blood to be diverted and the size of the natural artery 30.

The material of which the said connecting device 10 is made of can be hard, soft, flexible, or elastic. The material of which the sleeve is made out of should be of such a consistency as to be easily penetrated by a needle or staple yet be strong enough to hold the connecting device at the intended place or be made of a material that has holes 20 in the sleeve. The suture 40 attaches connecting device 10 to natural artery 30.

Artificial artery 18 or attachment of sleeve 16A of the connecting device 10 (FIG. 4 and 5) should be provided with curvatures of different degrees, mostly between 0 and 90 degrees, to give the surgeon using said connecting device 10 the opportunity to choose the most appropriate route for the artificial artery, for example parallel to the nonfunctional artery to be replaced.

The distance between sleeve and curvature should allow the surgeon to complete the suturing or stapling process. It is evident that the consumer should be provided with connecting devices of different inside diameters and also with different curvatures and with proper interrelationship between diameters of the natural and artificial arteries and the flow rate of blood. The top section 12 always protrudes the intima 34 when connecting device 10 is attached properly.

What is claimed is:

1. A connecting device for connecting an artificial artery to a natural artery in an end to side connection comprising:
   a tube having an inlet and an outlet opening;
   a sleeve positioned between the inlet opening and the outlet opening on the outside of said tube and attached to said tube;
   said sleeve having a surface configured to face the wall of the natural artery whereby a distance between said surface of said sleeve and said inlet opening is greater than a thickness of said wall of said natural artery which the connecting device is to be attached to.

2. The connecting device of claim 1 operably arranged whereby said tube penetrates said wall of said natural artery.

3. The connecting device of claim 1 wherein said sleeve surface is substantially parallel to the surface of said wall of said natural artery when operably arranged.

4. The connecting device of claim 1 operably arranged wherein said inlet opening is positioned between a center axis of said natural artery and an intima of said natural artery.

5. The connecting device of claim 1 operably arranged, such that a distance between said inlet opening of said tube and the surface of said sleeve, which is attached to said outside of said natural artery defines a substantial length of said tube projecting into the flowing blood of the natural artery.

6. The connecting device of claim 1 operably arranged, such that a distance between said inlet opening of said tube and the intima of the natural artery, which is attached to said outside of said natural artery defines a substantial length of said tube projecting into the flowing blood of the natural artery.

7. The connecting device of claim 1 operably arranged whereby said tube penetrates said wall of said natural artery in a substantially perpendicular direction.

8. The connecting device of claim 1 wherein said sleeve surface is substantially perpendicular to a portion of the tube that penetrates said natural artery.

9. A connecting device for connecting an artificial artery to a natural artery in an end to side connection comprising:
   a tube having an inlet and an outlet opening;
   a sleeve positioned between the inlet opening and the outlet opening on the outside of said tube proximal to said inlet opening and attached to said tube;
   said sleeve having a surface configured to face the wall of the natural artery whereby a distance between said surface of said sleeve and said inlet opening is greater than a thickness of said wall of said natural artery which the connecting device is to be attached to;
   said sleeve surface being substantially parallel to the surface of said wall of said natural artery when operably arranged;
   said inlet opening of said tube having a substantially smaller inside cross sectional area than that of the natural artery which said connecting device is to be attached to;
   said outlet opening of said tube having a substantially similar inside cross sectional area as the artificial artery which the connecting device is to be connected to;
   said inlet opening of said connecting device is positioned between a center axis of said natural artery and an intima of said natural artery when said connection device is operably arranged.

10. A connecting device for connecting an artificial artery to a natural artery in an end to side connection comprising:
    a tube having an inlet and an outlet opening;
    a sleeve positioned between the inlet opening and the outlet opening on the outside of said tube proximal to said inlet opening and attached to said tube;

means for attaching said connecting device to outside of said natural artery in an end to side connection operably arranged to enable said connecting device to divert blood from the natural artery to said artificial artery where said sleeve is positioned on the outside of a wall of said natural artery and said inlet opening is positioned within the flowing blood of the natural artery and beyond boundary layer blood flow region adjacent intima surface wall of the natural artery;

said sleeve having a surface configured to face the wall of the natural artery whereby a distance between said surface of said sleeve and said inlet opening is greater than a thickness of said wall of said natural artery which the connecting device is to be attached to;

said sleeve surface being substantially parallel to the surface of said wall of said natural artery when operably arranged;

said inlet opening of said tube having a substantially smaller inside cross sectional area than that of the natural artery which said connecting device is to be attached to;

said outlet opening of said tube having means to be connected to said corresponding artificial artery to couple said natural artery to said artificial artery;

said inlet opening of said connecting device is positioned between a center axis of said natural artery and an intima of said natural artery when said connection device is operably arranged;

a distance between said inlet opening of said tube and the surface of said sleeve, defines a substantial length of said tube projecting into the flowing blood of the natural artery when said connection device is operably arranged;

a distance between said inlet opening of said tube and the intima of the natural artery, defines a substantial length of said tube projecting into the flowing blood of the natural artery when said connection device is operably arranged.

11. A connecting device for connecting an artificial artery to a natural artery in an end to side connection comprising:

a tube having an inlet and an outlet opening;

a sleeve positioned between the inlet opening and the outlet opening on the outside of said tube proximal to said inlet opening and attached to said tube;

means for attaching said connecting device to outside of said natural artery in an end to side connection operably arranged to enable said connecting device to divert blood from the natural artery to said artificial artery where said sleeve is positioned on the outside of a wall of said natural artery and said inlet opening is positioned within the flowing blood of the natural artery and beyond boundary layer blood flow region adjacent intima surface wall of the natural artery;

said sleeve having a surface configured to face the wall of the natural artery whereby a distance between said surface of said sleeve and said inlet opening is greater than a thickness of said wall of said natural artery which the connecting device is to be attached to;

said sleeve surface being substantially parallel to the surface of said wall of said natural artery when operably arranged;

said inlet opening of said tube having a substantially smaller inside cross sectional area than that of the natural artery which said connecting device is to be attached to;

said outlet opening of said tube having a substantially similar inside cross sectional area as the artificial artery which the connecting device is to be connected to;

said outlet opening of said connecting device having means to be connected to said corresponding artificial artery to couple said natural artery to said artificial artery.

12. A connecting device that connects an artificial artery to a natural artery in an end to side connection comprising:

a tube having an open receiving end;

a sleeve attached around the artificial artery tube proximate its open receiving end adapted to be attached to a wall of a natural artery, for positioning the open receiving end of the artificial artery tube penetrating into the natural artery through the wall of the natural artery beyond boundary layer blood flow region adjacent intima surface wall of the natural artery for diverting blood flow.

* * * * *